United States Patent [19]

Schmeisser et al.

[11] Patent Number: 4,952,127
[45] Date of Patent: Aug. 28, 1990

[54] METHOD AND APPARATUS FOR SEPARATION OF HIGH-MOLECULAR-WEIGHT SUBSTANCES FROM A FLUID CULTURE MEDIUM

[75] Inventors: Holger Schmeisser, Göttingen; Heinz-Gerhard Köhn, Dransfeld, both of Fed. Rep. of Germany

[73] Assignee: Heraeus Sepatech GmbH, Osterode, Fed. Rep. of Germany

[21] Appl. No.: 403,708

[22] Filed: Sep. 6, 1989

[30] Foreign Application Priority Data

Sep. 19, 1988 [DE] Fed. Rep. of Germany ....... 3821771

[51] Int. Cl.$^5$ .............................................. B04B 11/02
[52] U.S. Cl. ......................................... 494/1; 494/10; 494/36; 494/37; 494/84
[58] Field of Search .................... 494/1, 10, 11, 22, 23, 494/27, 29, 35, 36, 37, 84, 85; 210/781, 782; 422/72

[56] References Cited

U.S. PATENT DOCUMENTS

| | | |
|---|---|---|
| 3,606,143 | 9/1971 | Stallman . |
| 3,814,306 | 6/1974 | Wutz . |
| 4,070,290 | 1/1978 | Crosby ................................... 494/11 |
| 4,093,118 | 6/1978 | Sinn . |
| 4,261,507 | 4/1981 | Bäumler . |
| 4,285,810 | 8/1981 | Kirkland ................................ 494/10 |
| 4,475,897 | 10/1984 | Bradtmoller .......................... 494/11 |
| 4,776,834 | 10/1988 | Müller . |

FOREIGN PATENT DOCUMENTS 3433611 3/1986 Fed. Rep. of Germany .

OTHER PUBLICATIONS

Intel Microcontroller Handbook 1985, Title & Contents Pages and p. 7-1.

Primary Examiner—Robert W. Jenkins
Attorney, Agent, or Firm—Frishauf, Holtz, Goodman & Woodward

[57] ABSTRACT

An improved method and apparatus for separating high-molecular-weight substances from cells suspended in liquid nutrient media, features continuous central monitoring and control of the process by a computer (22), and a way to combine the heretofore separate processes of first, separating media into solid and liquid components, and second, concentrating the proportion of high-molecular-weight components in the separated liquid. The media are conveyed by a first pump (3) to a centrifuge continuous flow rotor (2), which separates the solids from the liquid components and directs the latter to an intermediate reservoir (5), which sits on an electric scale (7) which is continuously monitored. From here they are fed to a filtration unit (9) in which the high-molecular-weight substances are separated and recycled through a feedback line (11), with the aid of a second pump (10), into the intermediate reservoir (5). The central computer and control unit (22) controls the centrifuge and pumps, monitors the scale (7) and pressure sensors (13), and adjusts the process parameters. An optical sensor (26) monitors the solids content at the centrifuge output (4).

20 Claims, 3 Drawing Sheets

METHOD AND APPARATUS FOR SEPARATION OF HIGH-MOLECULAR-WEIGHT SUBSTANCES FROM A FLUID CULTURE MEDIUM

Cross-reference to related U.S. Pats., the disclosures of which are hereby incorporated by reference: 3,606,143, 3,814,306, 4,093,118, 4,261,507, and 4,776,834.

Reference to literature: INTEL *Microcontroller Handbook*.

The invention relates generally to a method for separating solids, e.g. bacteria, yeasts, and animal and/or human cells, from liquid nutrient media and for enrichment of the proportion of high-molecular-weight substances contained in the remaining liquid. The liquid nutrient medium is collected from a fermentor or supply tank and separated by centrifuging into its solid and liquid components, after which, in an additional method step, the high-molecular-weight substances in the liquid components are enriched by filtration in a filtration unit. In addition, the invention relates to an apparatus for carrying out the method, having a fermentor or supply tank containing the liquid nutrient medium, connected by a first pump flowwise with the continuous flow rotor of a centrifuge, which has an outlet that leads to a tank.

BACKGROUND

Such methods, as well as corresponding devices are generally known. They are used for so-called cell harvesting, in other words, for separating and concentrating bacteria, for example, from liquid nutrient media. For this purpose, the centrifuges that are used are operated in the continuous flow mode. Solids are collected in the centrifuge rotor and the liquid components form the supernatant which is pumped out of the rotor and may be collected.

In this manner, very large quantities of suspension are centrifuged and separated. The liquid components, separated from the solids, are then separated into the high-molecular-weight and low-molecular-weight components in a separate process and/or a separate device using the so-called membrane filtration method. Various types of filters are used for the filtration technology, for example ultrafilters or microfilters which differ in the type of membrane used. Microporous membranes separate components in the 1/10 micron range, bacteria for example, while ultramembranes can separate much smaller components, proteins for example.

The known methods are also viewed as disadvantageous because they incorporate several separate method steps whose method parameters must be selected individually and therefore cannot be adjusted to one another, or can be adjusted only unsatisfactorily. In addition, these methods and/or the corresponding devices suffer from the disadvantage that the tanks with the components to be centrifuged or filtered must be moved around.

THE INVENTION

It is therefore an object of the present invention to provide a method and a device for separating high-molecular-weight substances from liquid nutrient media which avoids the above disadvantages and permits a process of simultaneous centrifugation and filtration.

Briefly, this objective is achieved in the method described above by virtue of the fact that, under central control, the continuous flow rotor of a centrifuge is continuously fed with liquid/solid suspension from the fermentor or supply tank until a predetermined desired or preset quantity of liquid components, stored centrally, is dispensed as a set value by the centrifuge into an intermediate reservoir, and by the fact that these liquid components are continuously fed directly into the filtration unit, followed by recycling of the high-molecular-weight components into the intermediate reservoir, with the filtration pressure being monitored centrally and a pump associated with the filtration unit being adjusted as a function of the pump rate. The supply to the centrifuge is controlled within preset values of the current or momentary or instantaneous filling level of the intermediate reservoir.

In a device, the goal is achieved by virtue of the fact that the tank serves as an intermediate reservoir and is connected with an ultrafiltration unit through a supply line and a return line. A second pump is located in the feed line to the filtration unit and the first pump, the second pump, and a centrifuge drive are connected by control lines with a central computer and control unit.

Liquid is drawn directly from the intermediate reservoir, continuously filled by the continuous flow rotor of the centrifuge, and fed to the filtration unit. At the same time, the intermediate reservoir, connected with the filtration unit through a return or feedback line, serves as a tank in which the high-molecular-weight substances of interest are enriched in the liquid phase. Since the removal of liquid components in the intermediate reservoir decreases as the concentration of high-molecular-weight components increases, the continuous flow rotor is controlled in such a way that, as a function of the oscillations in the filling level of the intermediate reservoir, the supply of liquid components from the continuous flow rotor to the centrifuge decreases.

With this arrangement, depending on the filling level of the intermediate reservoir, the centrifugation and filtration processes can be controlled and regulated in such fashion that a desired quantity of liquid enriched with high-molecular-weight substances can be collected in the intermediate reservoir. The level of concentration of high-molecular-weight substances at every point in time in the process can be determined. Losses or remaining quantities of liquids are not involved. Since all components, i.e. the centrifuge rotor, pumps, and filtration unit and associated valves and pressure sensors, are monitored and controlled centrally, all the parameters of the method can be determined.

Thus, in preferred embodiments of the method, the current instantaneous or "actual" filling level of the intermediate reservoir is constantly monitored centrally as an actual value and compared with the set value in order to adjust the flowrate from the continuous flow rotor of the centrifuge into the intermediate reservoir. In a very simple embodiment, such a filling level monitoring procedure can be carried out by an electronic scale, connected for example with a central computer and control unit, for example, the MCS-51 microcontroller. At the beginning of each centrifugation process, the scale is tared or the value of the empty tank that serves as the intermediate reservoir is stored centrally as a zero or starting value.

Since the continuous flow rotors used to separate solids from liquid components have only a limited capacity for solid components that remain in the rotor, it is advantageous continuously to determine the solids content of the liquid components transferred to the intermediate reservoir and, when a preset limit is exceeded, to interrupt the flow of suspension to the continuous flow rotor, since it may then be assumed that the continuous flow rotor is filled with solids, to the point almost of overflowing.

In order to ensure optimum adjustment of filtration for the filtration unit, the rate of the pump associated with the filtration unit should be controlled so that a filtration pressure stored centrally as a set value, compared with the pressure generated from the arithmetic mean between the pressure on the input side of the filtration unit and the pressure at the output discharging the high-molecular-weight substances from the filtration unit, is not exceeded. With a method of this kind, the filtration unit operates with its maximum efficiency and is simultaneously monitored to ensure that the filtration unit is not overloaded.

The end of the process can be indicated by the fact that, when a preset centrally stored maximum quantity of liquid components is exceeded in the intermediate reservoir, the flow is interrupted on the input side and on the output side of the filtration unit. At the same time the flow from the continuous flow rotor into the intermediate reservoir is stopped, since sufficient saturation of the liquid components loaded into the intermediate reservoir with high-molecular-weight substances has been achieved.

Another possibility for influencing the pressure in the area of the filtration unit is to adjust an additional throttle valve on the output of the filtration unit containing the high-molecular-weight substances. This throttle valve can generate a backpressure, thus reducing the flowrate through the filtration unit.

Since filters tend to clog, it is advantageous to wash out the filtration unit for cleaning purposes at long intervals by backflushing it with fluid taken from the intermediate reservoir. For such washing, the device has on the output side of the second pump, which feeds the liquid components to the filtration unit, a bypass line which can be shut off by means of a bypass valve in the line and through which liquid components can be fed to the filtration unit in a countercurrent flow. Since this backflow can cause the pressure conditions in the lines to and from the filtration unit to change, and normal shutoff valves provide sufficient sealing in one direction only, a backpressure valve is located on the output side of the second pump in the feed line to the filtration unit after the bypass line branches off, said valve acting opposite to the pumping direction of the second pump and preventing backflow of liquid components from the line on the inlet side of the filtration unit if such backpressure develops while the filtration unit is being rinsed. The pressure ratios on the input side and output side of the filtration unit are monitored by two pressure sensors in the feed line and the feedback line of the filtration unit, said monitoring devices constantly feeding the current pressure values to a central computer and control unit. An optical sensor, likewise connected with the computer and control unit, may be used to monitor the solids content of the liquid components transferred from the continuous flow rotor of the centrifuge to the intermediate reservoir. In order to terminate the separation process at a specific point in time, shutoff valves in the supply line to the filtration unit and in the feedback line between the filtration unit and the intermediate reservoir are desirable.

DRAWINGS

The method according to the invention, as well as the device according to the invention, will now be described with reference to the drawing, in which.

DETAILED DESCRIPTION

Figure 1:
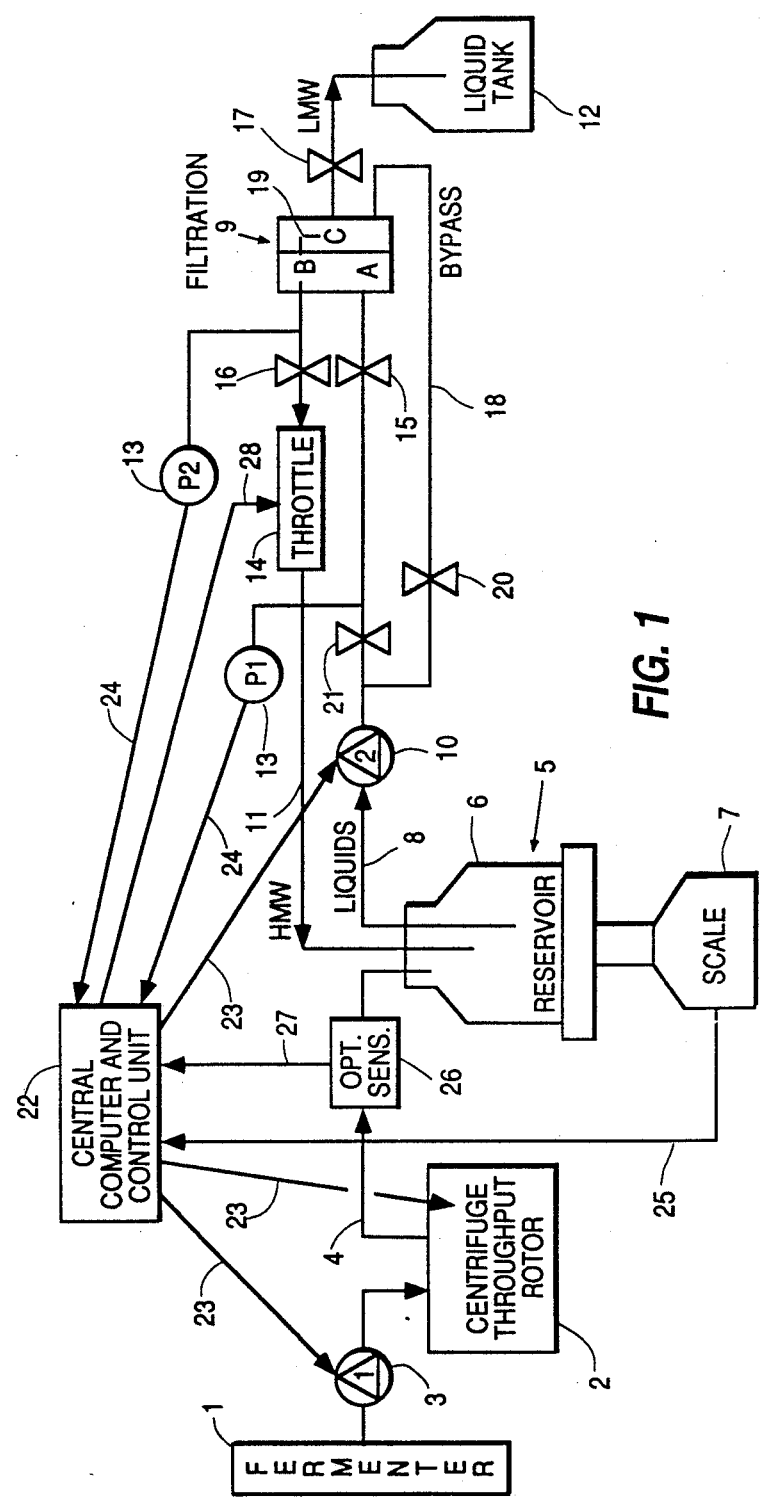
FIG. 1 is a schematic diagram of the design of a device according to the invention.

As FIG. 1 shows, the device has a fermenter 1 in which suspension is stored. This fermenter 1 is connected with the continuous flow rotor of a centrifuge 2 by a first pump 3, so that suspension can be continuously fed to the continuous flow rotor of centrifuge 2. Output 4 from centrifuge 2 leads to an intermediate reservoir 5, i.e. a tank 6 standing on an electronic scale 7. Electronic scale 7 constantly monitors the increase or decrease in weight of intermediate reservoir 5. Intermediate reservoir 5 is connected by a line 8 with a filtration unit 9. Liquid is fed through this line 8 by means of a second pump 10 in the supply line of filtration unit 9. The high-molecular-weight substances are retained in filtration unit 9 and the retentate returned through feedback line 11 to intermediate reservoir 6. The filtrate, depleted of high-molecular-weight substances, is fed by filtration unit 9 into a tank 12. In filtration unit 9, the inlet connected with supply line 8 is labeled A and the retentate output connected with feedback line 11 is labeled B, while the output which supplies the filtrate to tank 12 is labeled C.

A respective pressure sensor P1, P2, designated 13, is placed in each of lines 8 and in feedback line 11 in order to monitor the pressure in filtration unit 9 by means of these lines 8 and 11 and to adjust it if required. For such a pressure adjustment, a throttle valve 14 is incorporated into feedback line 11. In both line 8 and in feedback line 11, immediately upstream or downstream of inlet A or outlet B of filtration unit 9, a valve 15 or 16 is provided. Similarly, output C, for the filtrate leaving the filtration unit, has another valve 17 which can shut off the flow to tank 12.

In order to be able to clean the filter by backflushing, a bypass line 18 is used which runs from line 8 on the pressure side of second pump 10 to filtration unit 9 and supplies liquid from the supply line of filtration unit 9 as shown by broken line 19, thereby backflushing the latter, said liquid then being returned via outlet B and feedback line 11 into intermediate reservoir 5. This bypass line 18 can also be shut off by a bypass valve 20, which is only opened when filtration unit 9 is to be backflushed. As viewed from second pump 10, downstream from the point at which the bypass line branches off, a valve 21 is inserted into supply line 8, said valve acting opposite to the normal flow direction of the liquid in supply line 8, as indicated by the arrows, and designated to prevent backpressure from building up in supply line 8 when filtration unit 9 is rinsed. Such a backpressure valve 21 is needed since usually valves provide reliable sealing in one flow direction only.

The individual components of the device are monitored by a central computer and control unit 22 and the process itself is controlled. Computer 22 is preferably of the 8051 microprocessor family made by INTEL CORP. of Santa Clara, Cal. or respective second sources. Details are set forth in Intel's *Microcontroller Handbook* 1985, Chapters 7-11. First pump 3, second pump 10, and the drive of centrifuge 2 are connected by control lines 23 to computer and control unit 22; the two pressure sensors 13 are also connected with central computer and control unit 22 by a first and a second signal line 24. Scale 7, depending on the increase or decrease in weight, supplies corresponding signals through an additional signal line 25 to central computer and control unit 22. An optical sensor 26 is located in the line between outlet 4 of centrifuge 2 and intermediate reservoir 5, said sensor being connected by a third control line 27 with central computer/control unit 22. This sensor 26 monitors the increase in solids in the liquid transferred from the continuous flow rotor to intermediate reservoir 5 and interrupts the flow when a preset value is exceeded, since it can then be assumed that centrifuge 2 is not working properly, in other words, that the continuous flow rotor is overloaded with solids, so that the rotor must be emptied.

Valves 15, 16, 17, 20, and 21 are controlled by computer and control unit 22, and throttle valve 14 is controlled by additional control line 28.

Figure 2:
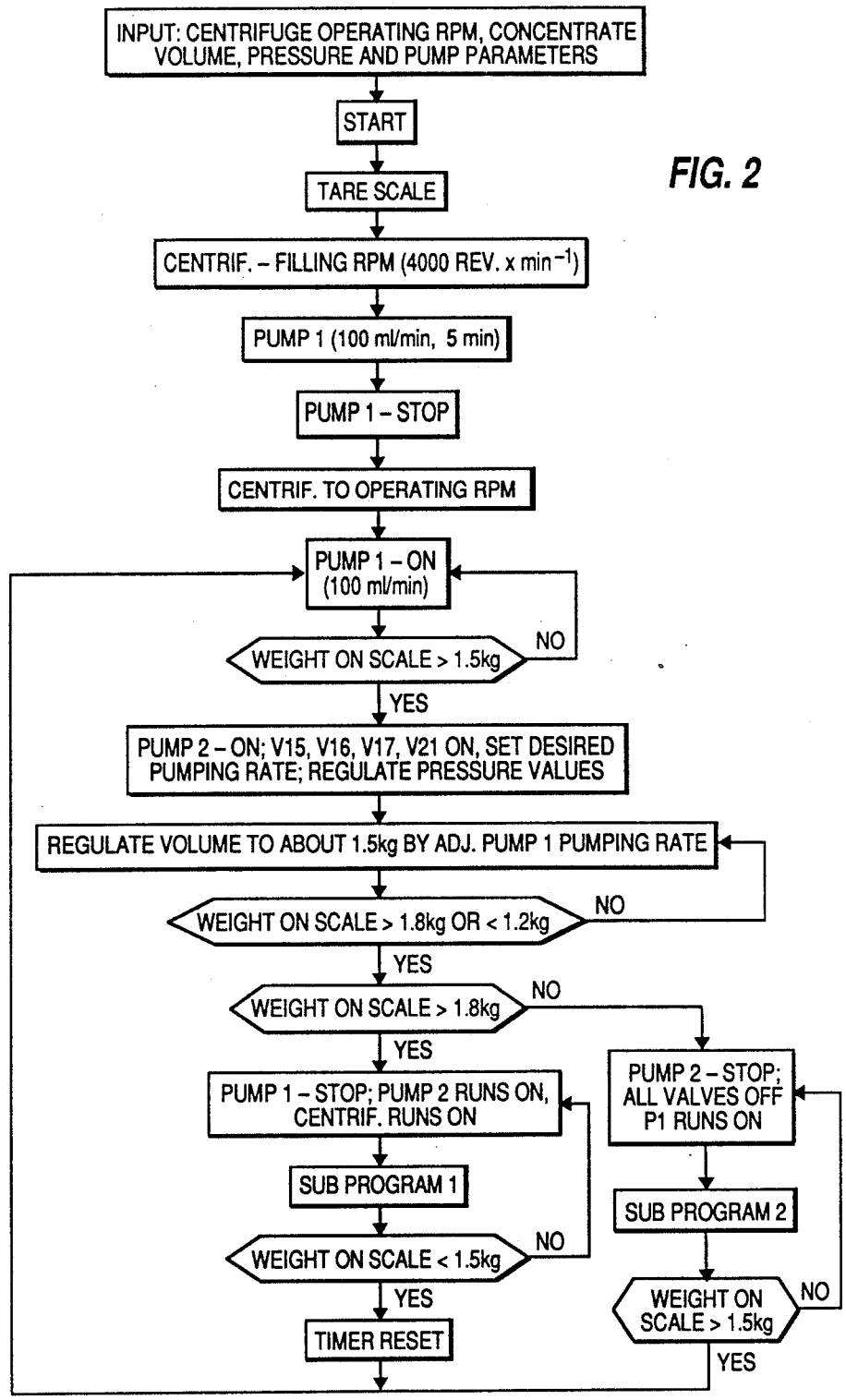
FIG. 2 is a flowchart showing a process that can be accomplished using the device in FIG. 1.

At the beginning of each process cycle, as shown in the flowchart in FIG. 2, input data are entered in the central computer in control unit 22, such as the operating rpm of centrifuge 2, the required concentrate volume in intermediate reservoir 5, the pressure distribution on the inlet side and discharge side of filtration unit 9, and the pumping capacity of second pump 10. After the system has been started, scale 7 is tared automatically, or the current reading of scale 7 is interrogated by computer and control unit 22 via additional signal line 25, when the scale has tank 6 resting on it, said tank 6 serving as intermediate reservoir 5, so that the increase in weight of this tank 6 can then be monitored.

After centrifuge 2 has accelerated to a filling rpm which, for example, may be 4000 rpm with an appropriate feedback via control line 23, first pump 3 is started via its control line 23, and then performs its pumping activity, for example, at a rate of 100 milliliters (ml)/min for a duration of 5 minutes, until the rotor of centrifuge 2 is filled with liquid taken from fermenter 1. Then first pump 3 is stopped, and started again after centrifuge 2 has been accelerated to its operating rpm, stored in computer and control unit 22 as input data.

First pump 3 is operated until scale 7 has detected, in intermediate reservoir 5, an increase in the weight of the liquid components separated from centrifuge 2 amounting to a preprogrammed value, e.g. 1.5 kilograms (kg). When a volume of liquid corresponding to this weight is reached in intermediate reservoir 5 or tank 6, second pump 10 is started, via control line 23 as well as additional signal lines, not shown in greater detail, which connect computer and control unit 22 with valves 15, 16, 17, and 21, and pump 10 is brought up to a preset pumping rate and valves 15, 16, 17, and 21 are opened. At the same time the pressure is regulated, using throttle valve 14, which is connected by additional control line 28 to central computer and control unit 22, as the two pressure sensors 13 are connected.

Figure 3:
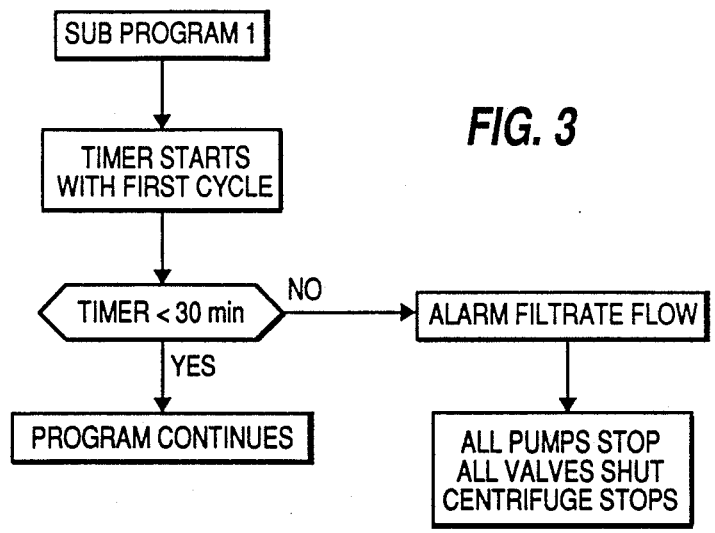
FIG. 3 is "subprogram 1" for the process shown in FIG. 2.
Figure 4:
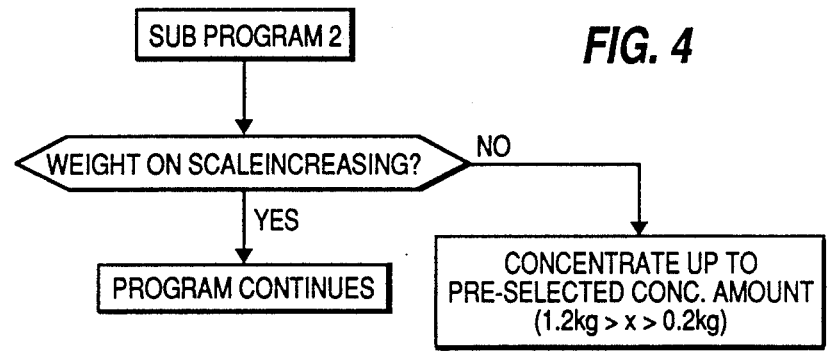
FIG. 4 is "subprogram 2" for the process shown in FIG. 2.

By presetting an upper and lower value, the volume in intermediate reservoir 5 is kept at an approximately constant filling level, for example 1.5 kg, with the rate of first pump 3 being changed accordingly. If a maximum filling level is reached in intermediate reservoir 5, corresponding for example to a weight of 1.8 kg, first pump 3 is stopped while second pump 10 and centrifuge 2 continue to run. Subprogram 1, as shown in FIG. 3, is then run. As long as the maximum filling level, for example equivalent to a weight of 1.8 kg, is not reached, the supply rate of second pump 2 is throttled or stopped and all valves are closed, after which subprogram 2 is run as shown in FIG. 4.

According to subprogram 1 (see FIG. 3) a timer is first started which is set, for example, to 30 minutes. As long as this time has not yet expired, the program runs as shown in FIG. 2, checking whether the weight on scale 7 is below 1.5 kg. If it is, the timer is reset and a jump made to the forward area of the flowchart. The first pump 3 is then switched on again. If, in subprogram 1, the time on the timer exceeds 30 minutes and the weight on scale 7 does not decrease any further, this indicates that filtration unit 9 may be clogged, so that an alarm indicating "filtrate flow" is given, and all pumps 3 and lo, as well as centrifuge 2, are stopped and all valves closed. After such an alarm is given, filtration unit 9 must be cleaned, for example by backflushing using bypass line 18. In the method shown in FIG. 2, in the decision diamond which tests whether the weight on the scale is more or less than 1.8 kg, if the weight has not been reached, second pump 10 is shut off and all valves are closed, first pump 3 continues operating and the shift is made to subprogram 2 as shown in FIG. 4. If these measures result in an increase in the weight on scale 7, the program is continued as shown in FIG. 2. If there is no weight increase on scale 7, only concentration takes place, as shown in subprogram 2 in FIG. 4, up to a preselected concentrate volume, for which purpose a separate subprogram can be run. If, according to subprogram 2, the weight on scale 7 is greater than 1.5 kg, a jump is made back to the upper range of the program and second pump 10 is immediately switched on and the valves opened.

Various changes and modifications are possible within the scope of the inventive concept.

We claim:

1. A method of separating solids, for example bacteria, yeasts, and animal and/or human cells, from liquid nutrient media and concentrating the proportion of high-molecular-weight substances contained in the remaining liquid, including taking liquid nutrient medium from a fermenter or supply tank (1), separating said medium by centrifugation (2) into its solid and liquid components and concentrating the proportion of high-molecular-weight substances in the liquid component simultaneously in a subsequent method step by filtration in a filtration unit (9), wherein the improvement comprises, centrally monitoring & controlling (22) each method step, continuously supplying a continuous flow rotor (2) of a centrifuge cells suspended in with liquid nutrient medium from the fermenter or supply tank (1) until a centrally stored preset value for the volume of liquid components has been supplied by the centrifuge into an intermediate reservoir (5), continuously feeding these liquid components from said intermediate reservoir (5) directly to the filtration unit (9), subsequently recycling (11) the high-molecular-weight components of said liquid components to the intermediate reservoir (5), centrally monitoring (22,24) pressure in the filtration unit (9) and adjusting (14,28) said filtration pressure as a function of the rate of a pump (10) associated with the filtration unit (9), and controlling the supply (3,23) to the centrifuge within preset values of the current filling level of the intermediate reservoir (5).

2. The method according to claim 1, further comprising reducing (3, 23) the flowrate of liquid nutrient medium into the centrifuge as the filling level of the intermediate reservoir (5) increases.

3. The method according to claim 1, further comprising increasing (3, 23) the flowrate of liquid nutrient medium into the centrifuge as the filling level of the intermediate reservoir (5) decreases.

4. The method according to claim 1, further comprising continuously centrally monitoring (7,22,25) as an actual value the current filling level of the intermediate reservoir (5).

5. The method according to claim 4, wherein the filling level is monitored by determining the change in weight of the intermediate reservoir (5).

6. The method according to claim 5, wherein the change in weight of the intermediate reservoir (5) is determined by a scale, and, at the beginning of a separation process, the scale is tared or the actual reading is stored centrally.

7. The method according to claim 1, wherein on the output side (4) of the continuous flow rotor, the solids content of the liquid components transferred to the intermediate reservoir (5) is determined (26) and, when a preset limit is exceeded, the flow of liquid nutrient medium to the continuous flow rotor is interrupted (3,23).

8. The method according to claim 1, further comprising storing centrally (22) a predetermined maximum filtration pressure, and controlling the pump rate of the pump (10) associated with the filtration unit (9) so that the arithmetic mean of the pressure on the inlet side (8) of the filtration unit and the pressure at the retentate output (11) of the filtration unit does not exceed said predetermined maximum filtration pressure.

9. The method according to claim 8, further comprising controlling the filtration pressure by adjusting an additional throttle valve (14) at the retentate side (11) of the filtration unit (9).

10. The method according to claim 1, further comprising storing centrally (22) a predetermined maximum quantity of liquid components in the intermediate reservoir (5), and when said maximum quantity is exceeded, interrupting (10, 14) the flows of components on the inlet side (8) and output side (11) of the filtration unit.

11. The method according to claim 1, further comprising monitoring pressure in said filtration unit (9) for indications of blockage, and automatically backflushing said filtration unit for clean using liquid drawn (18) from the intermediate reservoir (5).

12. A computerized apparatus for separating solids, for example bacteria, yeasts, and animal and/or human cells, from liquid nutrient media and for concentrating the proportion, of high-molecular-weight substances contained in the remaining liquid, comprising a supply tank (1) containing the liquid nutrient medium;

a supply tank output line including a first pump (3);

a continuous flow rotor (2) of a centrifuge, supplied by said first pump (3) through said tank output line;

said centrifuge rotor (2) having an output line (4) which leads into a tank (6) serving as an intermediate reservoir (5);

a filtration unit (9);

a liquid component supply line (8), including a second pump (10), connecting said intermediate reservoir to said filtration unit (9);

a high-molecular-weight substance feedback line (11) connecting said filtration unit (9) back to said intermediate reservoir (5); and a central computer and control unit (22), having input data lines (23,25,27) and output control lines (23,28), monitoring said intermediate reservoir and said filtration unit and controlling said first pump (3), said second pump (10), and said centrifuge continuous flow rotor (2).

13. A computerized apparatus according to claim 12, further comprising a respective pressure sensor (13), placed in each of said supply line (8) to filtration unit (9) and said feedback line (11) between said filtration unit (9) and said intermediate reservoir (5), said sensors being connected by a first and a second signal line (24) with said computer and control unit (22).

14. A computerized apparatus according to claim 12, wherein said intermediate reservoir (5) stands on an electronic scale (7), said scale being connected by an additional signal line (25) with computer and control unit (22).

15. A computerized apparatus according to claim 12, wherein an optical sensor (26) is positioned on the output side of continuous flow rotor in output (4) to intermediate reservoir (5), said sensor being connected by a third control line (26) with said computer and control unit (22).

16. A computerized apparatus according to claim 12, wherein a throttle valve (14) is placed in feedback line (11) between filtration unit (9) and intermediate reservoir (5), said throttle valve being connected by a further control line (28) with said computer and control unit (22).

17. A computerized apparatus according to claim 12, wherein a valve (15, 16) is placed in line (8) to filtration unit (9) as well as in feedback line (11) between filtration unit (9) and intermediate reservoir (5), said valves being controllable by said computer and control unit (22).

18. A computerized apparatus according to claim 12, wherein said filtration unit (9) has an additional output outlet for the filtrated depleted of high-molecular-weight substances, said outlet being closeable by an additional shutoff valve (17) controllable by said computer and control unit (22).

19. A computerized apparatus according to claim 12, wherein a bypass line (18) branches off on the output side of second pump (10), said line being closeable by a bypass valve (20) incorporated therein and feeding liquid components in a reverse flow to said filtration unit (9).

20. A computerized apparatus according to claim 19, wherein on the output side of second pump (10), a valve (20) is placed in supply line (8) to filtration unit (9) downstream from the point where bypass line (18) branches off, said valve (20) acting against the pumping direction of said second pump (10).

* * * * *